(12) United States Patent
Mortenson

(10) Patent No.: US 6,491,037 B1
(45) Date of Patent: Dec. 10, 2002

(54) TEMPERATURE INDICATING MOUTH GUARD

(75) Inventor: Daniel J. Mortenson, 200 Palomino La., Lino Lakes, MN (US) 55014

(73) Assignee: Daniel J. Mortenson, Lino Lakes, MN (US)

( * ) Notice: Subject to any disclaimer, the term of this patent is extended or adjusted under 35 U.S.C. 154(b) by 0 days.

(21) Appl. No.: 09/975,702

(22) Filed: Oct. 10, 2001

(51) Int. Cl.[7] .................................................. A61C 5/14
(52) U.S. Cl. ....................................... 128/859; 128/860
(58) Field of Search .................................. 128/846, 848, 128/859–862; 73/356; 602/902

(56) References Cited

U.S. PATENT DOCUMENTS

| | | | |
|---|---|---|---|
| 3,733,905 A | * | 5/1973 | Bremer .................... 73/356 |
| 4,028,111 A | | 6/1977 | Iwasaki et al. |
| 4,447,164 A | | 5/1984 | Berndt |
| 4,511,265 A | | 4/1985 | Berndt |
| 4,955,393 A | | 9/1990 | Adell |
| 5,051,476 A | | 9/1991 | Uji et al. |
| 5,085,607 A | | 2/1992 | Shibahashi et al. |
| 5,176,704 A | | 1/1993 | Berndt |
| 5,219,625 A | | 6/1993 | Matsunami et al. |

* cited by examiner

*Primary Examiner*—Michael A. Brown
(74) *Attorney, Agent, or Firm*—Kagan Binder, PLLC

(57) ABSTRACT

A mouth guard is provided for protection from physical injury and for monitoring body temperature of the wearer. The mouth guard comprises an element comprising a color-changing component. The color-changing component changes color to indicate a preselected temperature state of the mouth guard. By visual inspection of the mouth guard, the wearer or a third party is provided with an objective indication that the person wearing the mouth guard is in danger of experiencing heat related illness. Methods of use and of manufacture of such mouth guards are also provided.

18 Claims, 1 Drawing Sheet

TEMPERATURE INDICATING MOUTH GUARD

FIELD OF THE INVENTION

The present invention relates to mouth guards. More specifically, the present invention relates to mouth guards having the ability to indicate a preselected temperature state.

BACKGROUND OF THE INVENTION

People of all ages engage in athletics to maintain their own personal desired level of physical condition, and to participate in enjoyable sports activities both on the recreational and professional level. When engaging in such activities, heat is produced during exercise. This excess heat must be eliminated from the body to maintain appropriate body temperature. Heat is transferred from the muscles first to the body core, which then transfers the heat through the blood to outer surfaces of the body. Heat is then transferred to the environment by convection and radiation, primarily through evaporation of sweat in order maintain the appropriate body temperature. Under certain conditions, such as extreme outdoor temperatures or a lack of sufficient fluid in the body to generate sweat, the core body temperature of an athlete may be quickly elevated to a physically dangerous or even lethal level.

As the body temperature of the person participating in athletic activities increases, the person may first experience heat cramps. While heat cramps may be painful, they are not considered to be a physically dangerous situation. Further increase of the core body temperature may lead to heat exhaustion, which is generally recognized as a situation that occurs when a person's body temperature increases to over 102° F. At this stage, the athlete may feel nausea, extreme fatigue, dizziness, vomiting and fainting. This condition is serious, and should be carefully monitored.

When the body's heat dissipating systems are overwhelmed, heat stroke may result. This is a life-threatening condition. At advanced stages of heat stroke, even emergency medical care may not be sufficient to save the person's life. At a body temperature of about 105 degrees or higher, a person may experience a variety of symptoms, possibly including seizures and unconsciousness. Every year a certain number of athletes, including professional athletes, college-level athletes and recreational athletes, die from heat stroke. These deaths are avoidable if steps are taken to avoid heat stroke. Unfortunately, persons suffering from heat related illnesses also often experience confusion. This confusion may lead to a lack of judgment that impairs their ability to make clear and rational decisions about their own health. This dangerous situation is further compounded by situations where a peer pressure environment exists, thereby encouraging or requiring the athlete to continue in the athletic activities rather than take care of their own health. An objective early warning system would be useful in alerting the athlete or those around the athlete that danger of heat related illnesses is imminent.

Mouth guards have been used for many years to protect athletes from physical injury to the teeth, gums, and other tissues of the mouth. The U.S. Pat. No. 4,955,393 discloses a mouth guard with conformable arch liners. U.S. Pat. No. 5,051,476 discloses an improved mouth guard composition comprising and ethylene-vinyl acetate copolymer and a thermoplastic polycaprolactone having a molecular weight of 10,000–100,000 optionally with polyvinyl acetate, colorants and perfumes.

Temperature responsive color-changing materials have been known in various uses. U.S. Pat. No. 4,447,164 discloses a temperature responsive pacifier assembly, which comprises a liquid crystal material in a liquid that is responsive to a temperature above about 100° F. This assembly is designed to indicate an abnormal temperature condition of an individual utilizing the pacifier assembly. U.S. Pat. No. 5,085,607 discloses a toy set having at least one section which bears a color memory dye of an electron supplying organic coloring compound, an electron accepting compound and an ester. U.S. Pat. No. 5,219,625 discloses a thermochromatic laminate member and toy utilizing the same.

SUMMARY OF THE INVENTION

A mouth guard is provided for insertion into the oral cavity during physical activity for protection from physical injury. The mouth guard comprises an element comprising a color-changing component. The color-changing component changes color to indicate a preselected temperature state of the mouth guard. Methods of use and of manufacture of such mouth guards are also provided.

DETAILED DESCRIPTION OF THE INVENTION

Figure 1:
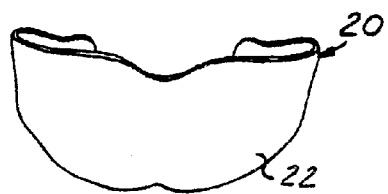
FIG. 1 is a front perspective view of a mouth guard embodying principles of the invention.

The mouth guard of the present invention provides significant benefits to users thereof. During the time that the mouth guard operates in its ordinary everyday function of providing protection against physical injury of teeth, gums and other tissues of the mouth, it additionally provides an objective early warning function of temperature indication for the user. As the athlete uses the mouth guard of the present invention in its ordinary function, he or she will remove the mouth guard at appropriate break times during the athletic activity. This removal provides the opportunity for the athlete or an observer to note and recognize temperature change that may indicate danger of physical illness related to heat. Because this temperature indicator is integral with an essential piece of injury protection equipment, no additional step need be taken to monitor the body temperature of the athlete. Further, because the temperature indication is objective in nature, the presence of such indication allows the athlete and/or any third party, such as a coach, to excuse further athletic activity until the temperature situation is corrected. The present invention therefore provides an effective temperature monitoring system for the busy athlete or athlete under severe pressure to perform that may not otherwise realize the presence of a dangerous temperature situation.

As its primary function, the mouth guard of the present invention protects against injury accidents, such as damage or fracture of the teeth and jawbones, that may occur during the course of physical activity. Such injury accidents occur frequently in sport games such as boxing, rugby, soccer, hockey, football and the like, and may also occur during individual athletic activities, such as skateboarding or in line skating, skiing, mountain biking and the like. The mouth guard of the present invention may utilize any structural design that is appropriate for protection of the tissues of the mouth.

The mouth guard of the present invention is constructed from materials having suitable strength to protect against external forces and to have an effect of cushioning external pressures. Selection of such materials is known in the art, and may include, for example, materials such as polyvinyl chloride (PVC) and ethylene/vinyl acetate copolymers (PVAc-PE). One such construction is the combination of ethylene/vinyl acetate copolymer and thermoplastic polycaprolactone as disclosed in U.S. Pat. No. 5,051,476, the disclosure of which is incorporated herein by reference.

Mouth guards of the present invention may be provided in generally one of three formats. The mouth guard may be of the ready-made, mouth-formed or custom-made varieties. Mouth guards of the ready-made, commercial variety have a pre-set size and configuration. Examples of mouth guards of the ready-made variety (without the additional temperature indication features as explained below) are typically sold at most sporting goods stores and are made of rubber or polyvinyl. These mouth guards are the least expensive of the varieties available, but are also the least effective in protecting against injury.

Mouth-formed guards, also called "boil and bite" guards, are generally soft or softenable pre-formed guards that can be shaped to the contours of the teeth and allowed to harden. Preferably, this shaping is done by a dentist or dental professional, although products that may be adapted by the user at home are also possible.

Custom-made mouth guards are professionally designed by the dentist or dental professional from a cast model of the user's teeth. Custom guards offer the best possible fit and protection against physical injury. Additionally, custom guards generally are more secure in the mouth and exhibit less interference with speech or breathing.

Mouth guards of the present invention may be fitted to provide coverage of only teeth of the upper jaw or of the lower jaw, or in the alterative maybe fitted so that the athlete bites into the mouth guard to immobilize teeth of both the upper and lower jaw. The mouth guard may extend all the way to the back of the mouth to cover back teeth, or alternatively may extend only to the extent required to provide suitable protection corresponding to the physical activity to be engaged in by the athlete.

The mouth guard of the present invention further comprises an element comprising a color-changing component that changes color to indicate a preselected temperature state of the mouth guard. This element may be in any physical configuration, such that when a color change occurs the user or third party may observe the indication of the temperature state of the mouth guard. In a preferred embodiment, the element is the entire mouth guard, and the color-changing component is dispersed throughout material of the mouth guard. In this embodiment, the color-changing component is any component as discussed below, which is mixed with the resin from which the mouth guard is formed such that the entire device appears to change color to indicate the temperature state of the mouth guard. In an alternative embodiment of the present invention, the element comprising the color-changing component is a coating on at least a surface of the mouth guard. In another embodiment of the present invention, the element is in the shape of a character, sign, figure, or pattern on a surface of the mouth guard. Thus, when the mouth guard of the present invention reaches a predetermined temperature state, one or more surfaces of the mouth guard may change appearance such that a pattern such as the word "danger " becomes visible. In yet another embodiment, the element is a separate structure, such as a piece, later, band or the like, that is securely fixed to a conventional mouth guard. The element may be so fixed by an interlocking feature, adhesive, fastener (such as a screw) or the like, so that in ordinary use the element does not separate from the mouth guard. In one aspect of this embodiment, conventional existing mouth guards may be retrofitted with an element as described herein.

The mouth guard of the present invention is preferably provided with a color-change functionality that indicates the temperature of the mouth guard at a preselected temperature that indicates a rise in body temperature of a subject wearing the mouth guard to a level to indicate danger of illness due to heat. More preferably, the color change occurs at a preselected temperature that indicates a rise in body temperature of a subject wearing the mouth guard to a level to indicate danger of heat stroke.

In a particularly preferred embodiment, the preselected temperature of color change of the element is selected to show that the body temperature of a subject wearing the mouth guard is at or above 102° F. In another particularly preferred embodiment, the preselected temperature of color change of the element is selected to show that the body temperature of a subject wearing the mouth guard is at or above 104° F. In yet another particularly preferred embodiment, the preselected temperature of color change of the element is selected to show that the body temperature of a subject wearing the mouth guard is at or above 105° F. These preselected temperature levels correspond to body temperatures that represent various degrees of danger in increasing body temperature, wherein the risk of physical harm to health increases with increasing temperature.

In a particularly preferred embodiment, the mouth guard of the present invention contains a plurality of elements comprising color changing components, wherein each of the elements indicates that the body temperature of the user of the mouth guard is at or above a preselected temperature that is different from at least one of the other elements. In this embodiment, the mouth guard may provide sequential, progressive and increasing warning as to the increasing risk of physical harm to health. For example, the mouth guard may appear to be white at ordinary body temperature, a bright yellow color at a temperature of 102° F., and red at a temperature of 104° F. The various elements may be oriented in a side-by-side on the mouth guard, such that, for example in the embodiment described above the yellow color may appear as a band alongside the red color. Optionally, the elements may be oriented on top of each other, so that in the embodiment as described above, the yellow color elements may be located below the red color element. In use, as temperatures approach the most dangerous level, the uppermost red color element would obscure the yellow colored element lying below.

For purposes of the present invention, color-changing includes any visible change of the visual perception of the mouth guard, including changes in the grayscale or tone of the mouth guard. Preferably, the color indication is sufficient in nature that it may be observed by ordinary visual perception from a distance greater than 5 feet away from the mouth guard. More preferably, the color indication is sufficiently vivid in nature that may be observed by ordinary visual perception at a distance greater than 10 feet away from the mouth guard, and most preferably at distances greater than 50 feet away.

In one embodiment of the present invention, the change in color of the color-changing component is an irreversible color change. In this embodiment of the invention, the mouth guard will provide a permanent record of exposure to a high temperature. In a more preferred embodiment, the change in color of the color-changing component is a reversible color change. In this embodiment, the mouth guard may be used over and over again, even after exposure to extremely high temperatures. This embodiment may find most practical utility, since there is no concern of exposure of the mouth guard to excessively high temperatures during shipping or when located in extremely hot climate situations.

The color-changing component may be any material that perceptively changes color, shade or tone as the temperature of the mouth guard increases. Examples of preferred such color changing component materials include dyes, pigments, chemical solutions, liquid crystals, or any other materials that changes visual perception as its temperature increases.

Examples of such color change materials include thermochromic materials comprising an electron-supplying organic coloring compound and an electron-accepting compound. Examples of such materials are disclosed in U.S. Pat. No. 5,085,607 and U.S. Pat. No. 5,219,625, disclosures of which are incorporated herein by reference. Particularly preferred to record materials are those that are coated on eating utensils for babies and young children, which serve as temperature indication systems to show whether the food to be served to the children is inappropriately hot. The temperature at which these materials indicate a color change may be adjusted by dilution or by chemical sensitization, in a manner known to those of skill in this art.

Liquid crystal compositions may also be used as the color changing component. Examples of compositions of this nature are disclosed in U.S. Pat. Nos. 4,511,265; 5,176,704; and 4,447,164, the disclosures of which are incorporated herein by reference. Chloresteric liquid crystals are preferred since such chloresteric liquid crystals are non-toxic and readily passed through the body if accidentally ingested by the mouth guard user. One skilled in the art will appreciate that the composition of the liquid crystal may be formulated to effect different color changes, e.g. green to black, or some other color-changing protocol. Once removed from the mouth of a user, the liquid crystal material will resume its initial color after a predetermined time period at ambient room temperature.

The color changing component may be dispersed in a medium containing a binder, and can be provided in the form of a coloring material such as ink, pigment or paint, so that the mouth guard surfaces or any desired portion of such surfaces can be treated with the color changing component by any suitable conventional method such as coating, spraying, printing and dipping.

The binder may be a conventionally-used binding agent such as natural or synthetic rubbers and waxes. The kind of the binder to be used is suitably selected depending on the material of the toy set.

The color changing component may alternatively be placed within microcapsules. The microencapsulated component may be disbursed as such within the material of the mouth guard, or may be mixed with a binder in a dispersed condition to form a color layer. Preferably, the content of the microencapsulated pigment in the color layer is provided in an amount sufficient to obtain optimal thermochromatic effects.

Generally, liquid crystal materials displaying the desired color-changing protocol herein described generally are adversely affected by the elastomeric material of the mouth guard and thus cannot be formulated, per se, in the elastomeric material of the mouth guard assembly although some liquid crystals may exist which may be included in such a formulation. Microencapsulation of the liquid crystal materials would permit formulation with the elastomeric material of the mouth guard.

In order to provide protection to the present mouth guard, a transparent resin film of an acrylic, a water-repellent or other transparent resin may be formed as an overcoat layer over all or some portion of the mouth guard. This overcoat layer may optionally enhance the glossiness, stain resistance and water resistance etc. of any overcoated surface of the present mouth guard. Additionally, an overcoat layer may provide protection from removal by solvation or by frictional action of the color changing component from the mouth guard.

Additional additives, such as stabilizers, antioxidants, ultraviolet-absorbing agents, and the like may be provided in the mouth guard material, in the element, or in any overcoat composition in order to extend the functional life of the mouth guard, such as by improving its resistance to fading in light, preserving the shock absorbing characteristics of the mouth guard, preserving or adjusting the sensitivity of the color-changing component, and the like.

Once the mouth guard of the present invention changes color indicating an abnormal temperature level as a result of use by an individual, resort to a mercurial thermometer or other precise temperature measurement technique is generally contemplated as a part of a use protocol of use of the present invention. The device of the present invention is contemplated as providing an early warning sign of potential illness due to heat. The mouth guard of the present invention is considered to be a useful device to be used as part of an overall program of medical awareness to protect the well-being and health of individuals participating in athletic endeavors.

Figure 2:
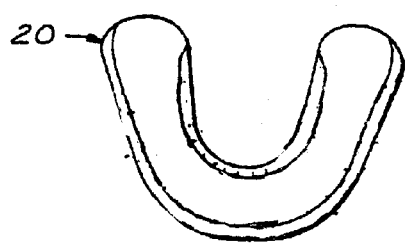
FIG. 2 is a top plan view of the mouth guard of FIG. 1.

Turning now to the drawings, FIGS. 1 and 2 illustrate an embodiment of mouth guard 20 according to principles of the invention. The mouth guard comprises a body 22 whose shape corresponds generally to that of the upper and lower arches. The color changing component that changes color to indicate a preselected temperature state of the mouth guard is preferably dispersed throughout the mouth guard structure.

Figure 3:
FIG. 3 is a front perspective view of another embodiment of a mouth guard embodying principles of the invention.

FIG. 3 shows a perspective view of a mouth guard 30, comprising a body 32 with a pattern 34 indicating that the mouth guard is at a predetermined temperature state.

It will be appreciated that numerous modifications and variations of the invention are possible in light of the above teachings, and therefore the invention may be practiced otherwise than as particularly described.

I claim:

1. A method of monitoring the body temperature of a person engaged in athletic activity, said method comprising
   a. providing a person to be engaged in athletic activity with a mouth guard for insertion into the oral cavity during physical activity for protection from physical injury, said mouth guard comprising an element comprising a color-changing component that changes color to indicate a preselected temperature state of the mouth guard,
   b. having said person wear said mouth guard during athletic activity,
   c. visually inspecting said mouth guard to determine whether said mouth guard is at or above a preselected temperature.

2. The method of claim 1, wherein the preselected temperature is selected to indicate a rise in body temperature of a subject wearing the mouth guard to a level to indicate danger of illness due to heat.

3. The method of claim 1, wherein the preselected temperate is selected to indicate a rise in body temperature of a subject wearing the mouth guard to a level to indicate danger of heat stroke.

4. The method of claim 1, wherein the preselected temperature is selected to indicate that the body temperature of a user wearing the mouth guard is at or above 102° F.

5. The method of claim 1, wherein the preselected temperature is selected to indicate that the body temperature of a user wearing the mouth guard is at or above 104° F.

6. The method of claim 1, wherein the preselected temperature is selected to indicate that the body temperature of a user wearing the mouth guard is at or above 105° F.

7. The method of claim 1, wherein the color-changing component is a thermochromatic ink.

8. The method of claim 1, wherein the color-changing component is a thermochromatic pigment.

9. The method of claim 1, wherein the color-changing component is a liquid crystal material.

10. The method of claim 1, wherein the liquid crystal material comprises a chloresteric liquid crystal.

11. The method of claim 1, wherein the element is the entire mouth guard, and the color-changing component is dispersed throughout the mouth guard.

12. The method of claim 1, wherein the element is a coating on at least a major surface of the mouth guard.

13. The method of claim 1, wherein said mouth guard comprises an additional protective coating over the coating that is the element.

14. The method of claim 1, wherein the element is in the shape of a charter sign, figure, or pattern on a surface of the mouth guard.

15. The method of claim 1, wherein the change in color of the color-changing component is a reversible color change.

16. The method of claim 1, wherein the change in color of the color-changing component is an irreversible color change.

17. The method of claim 1, wherein the element is a separately provided structure securely attached to the mouth guard.

18. The method of claim 1, said mouth guard comprising a plurality of said elements, wherein at least one of the elements indicates that the body temperature of the user of the mouth guard is at or above a preselected temperature that is different from a preselected temperature at least one of the other elements.

* * * * *

UNITED STATES PATENT AND TRADEMARK OFFICE
CERTIFICATE OF CORRECTION

PATENT NO. : 6,491,037 B1
DATED : December 10, 2002
INVENTOR(S) : Daniel J. Mortenson It is certified that error appears in the above-identified patent and that said Letters Patent is hereby corrected as shown below:

<u>Column 7,</u>
Lines 3-4, "temperate" should be -- temperature --.
Line 22, "claim 1" should be -- claim 9 --.

<u>Column 8,</u>
Line 3, "claim 1" should be -- claim 12 --.
Line 7, "charter" should be -- character --.

Signed and Sealed this

Twenty-second Day of April, 2003

JAMES E. ROGAN
*Director of the United States Patent and Trademark Office*